United States Patent [19]
Morgan

[11] Patent Number: 6,016,059
[45] Date of Patent: Jan. 18, 2000

[54] DEFIBRILLATOR SYSTEM CONDITION INDICATOR

[75] Inventor: Carlton B. Morgan, Bainbridge Island, Wash.

[73] Assignee: Heartstream, Inc., Seattle, Wash.

[21] Appl. No.: 08/467,062

[22] Filed: Jun. 6, 1995

Related U.S. Application Data

[62] Division of application No. 08/063,631, May 18, 1993, abandoned.

[51] Int. Cl.[7] .................................................... G01R 27/26
[52] U.S. Cl. .............................................................. 324/556
[58] Field of Search ................................... 324/537, 127, 324/556; 128/706; 607/6–8

[56] References Cited

U.S. PATENT DOCUMENTS

| | | | |
|---|---|---|---|
| 3,747,605 | 7/1973 | Cook ........................................ | 324/142 |
| 3,798,542 | 3/1974 | Dempsy ................................... | 324/133 |
| 3,983,476 | 9/1976 | Konopasek .............................. | 324/115 |
| 4,628,935 | 12/1986 | Jones et al. . | |
| 5,097,830 | 3/1992 | Eikefjord ................................ | 128/772 |
| 5,201,865 | 4/1993 | Kuehn ..................................... | 128/772 |
| 5,231,987 | 8/1993 | Robson . | |
| 5,384,544 | 1/1995 | Flugstad et al. ........................ | 324/678 |
| 5,399,980 | 3/1995 | Rashford ................................ | 324/678 |
| 5,453,698 | 9/1995 | Williams et al. ....................... | 324/537 |
| 5,554,173 | 9/1996 | Lemole ................................... | 324/149 |

FOREIGN PATENT DOCUMENTS

| | | |
|---|---|---|
| 47386/93 | 3/1994 | Australia . |
| B-49189/93 | 6/1994 | Australia . |
| 0472411 A1 | 2/1992 | European Pat. Off. . |
| 0551746 A2 | 7/1993 | European Pat. Off. . |
| 2172681 | 9/1973 | France . |
| 2712352 A1 | 9/1978 | Germany . |

OTHER PUBLICATIONS

Bennett, et al. "Portable Defibrillator–Monitor for Cardiac Resuscitation" *Hewlett–Packard Journal* pp. 22–27 (Feb. 1982).

Blomfield "A cost effective defibrillator analyser" *Australasian Physician & Engineering Sciences in Med.* 11(2):116–117 (1988).

*Primary Examiner*—Maura Regan

[57] ABSTRACT

A defibrillator and electrode system that gives the user a visible and/or audible indication of the condition of the electrodes and other parts of the defibrillator system prior to deployment of the electrodes and use of the defibrillator. In a preferred embodiment of the method of this invention, a patient simulation and analyze circuit within the defibrillator periodically tests the condition of the system and provides the user with a visual indication of the system's condition.

11 Claims, 6 Drawing Sheets

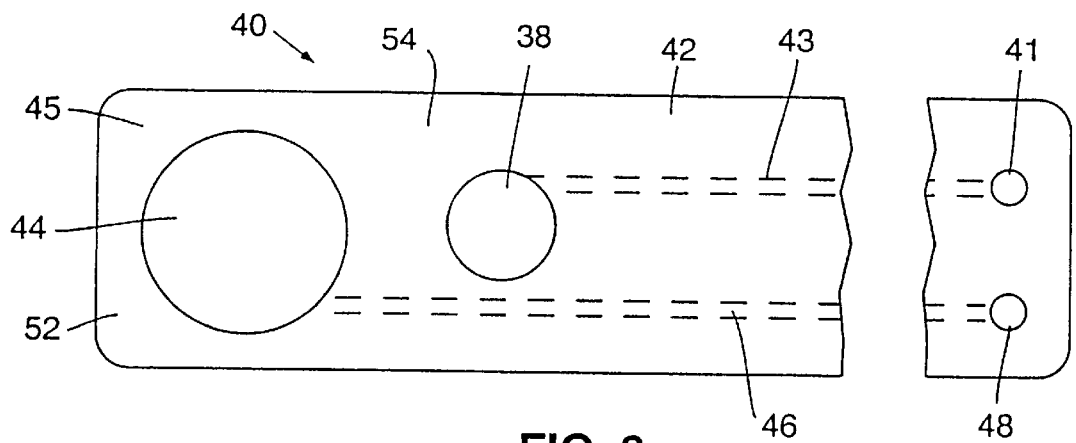
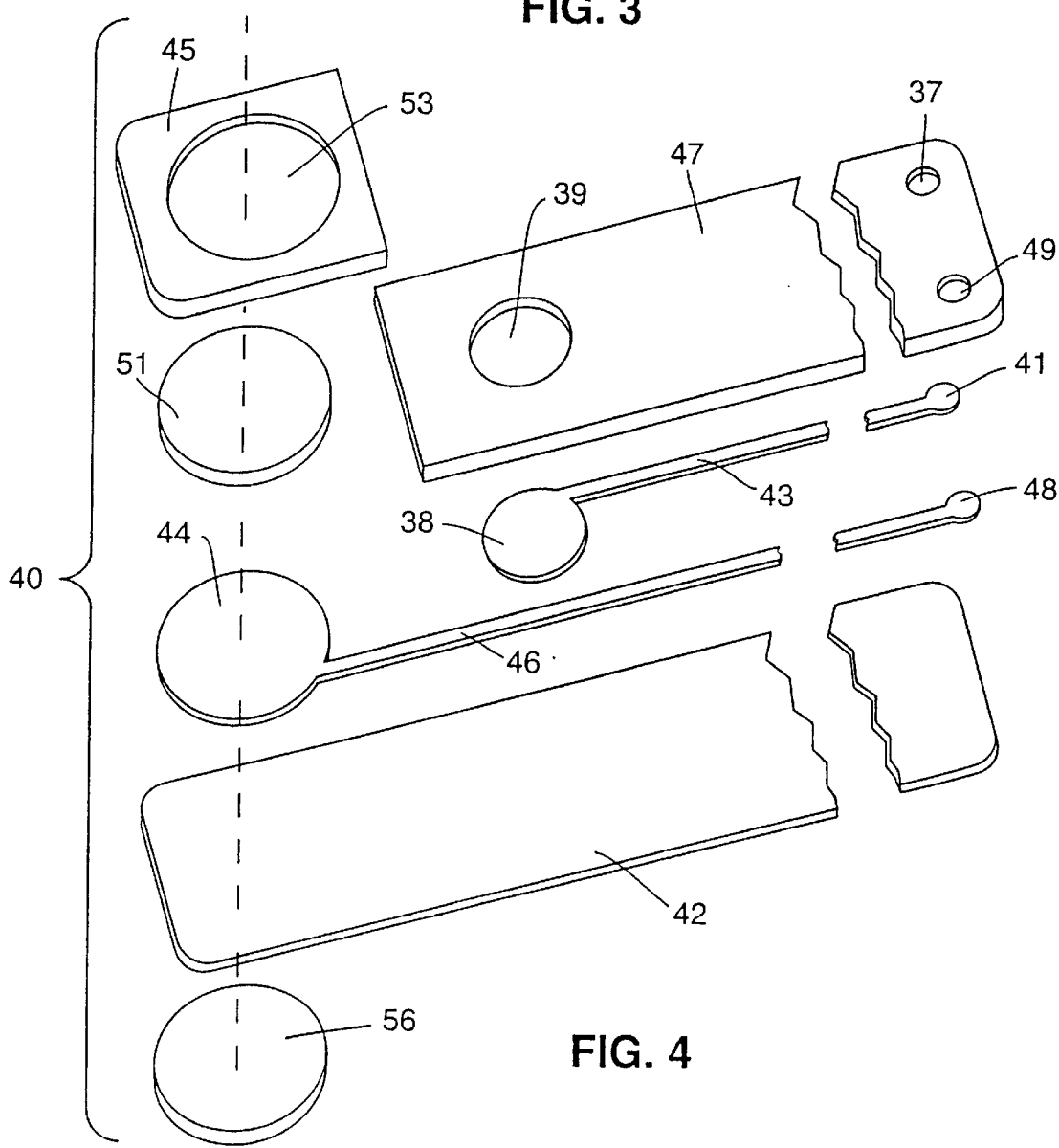
FIG. 3
FIG. 4

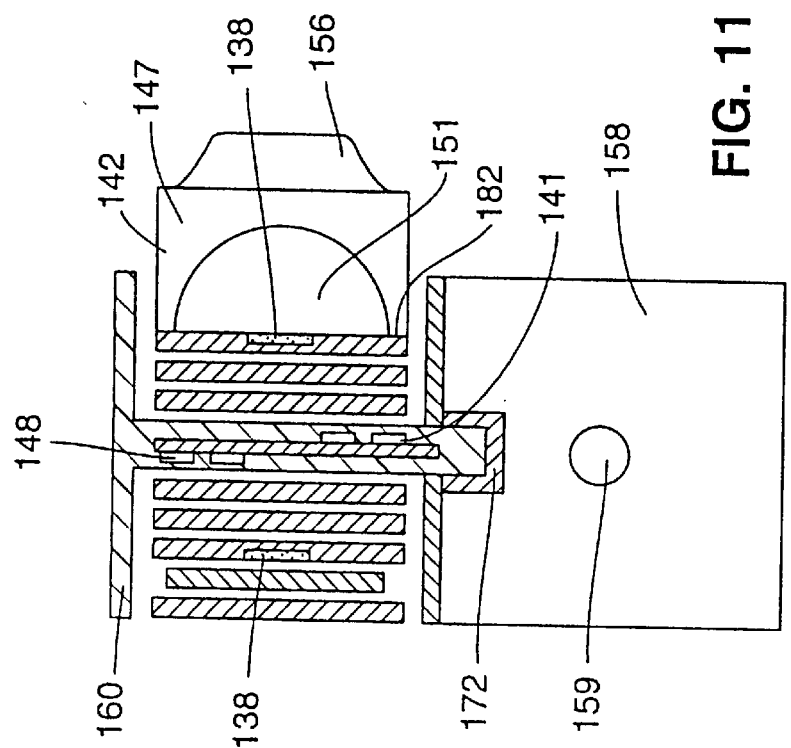
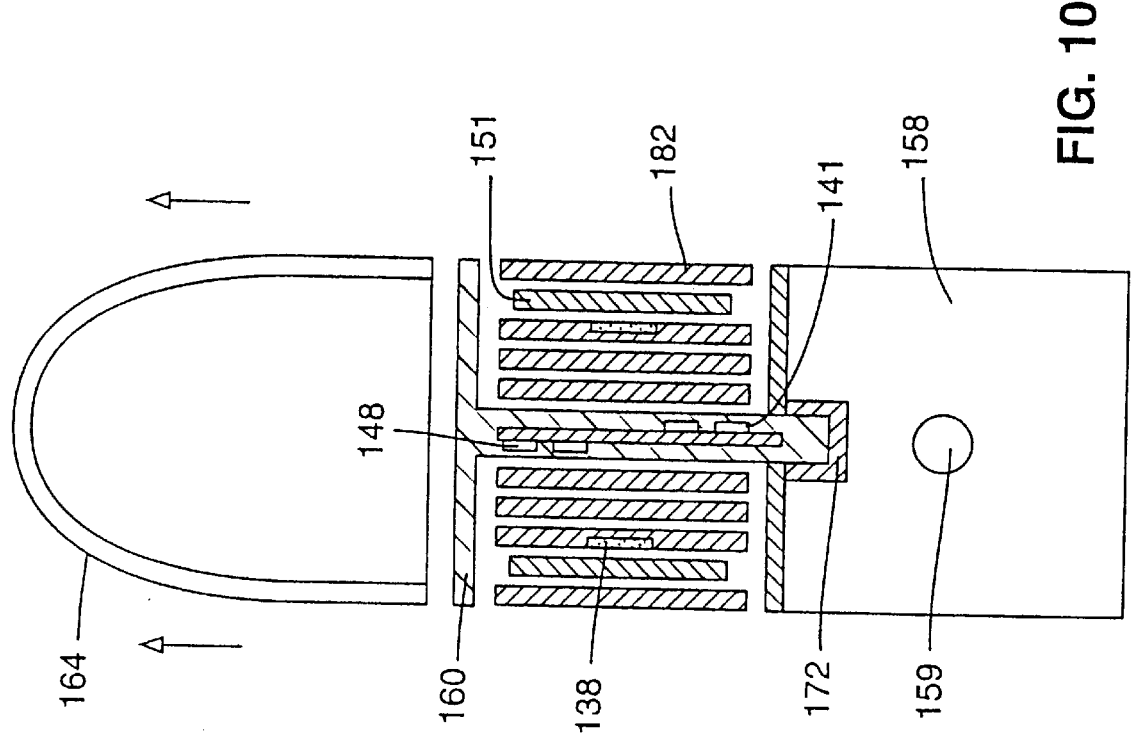

DEFIBRILLATOR SYSTEM CONDITION INDICATOR

This appln is a Division of Ser. No. 08/063,631 filed May 18, 1993, abnd.

BACKGROUND OF THE INVENTION

This invention relates generally to a method and apparatus for testing medical electrode systems and, in particular, to a method and apparatus for testing the operating condition of defibrillators and defibrillator electrodes and for providing the user with an indication of the system's condition.

Defibrillators apply voltage pulses to a patient's heart in response to a life-threatening condition such as cardiac arrest. External defibrillators deliver the voltage pulse through a pair of electrodes placed on the patient's chest or back by the attending medical personnel. The primary components of a defibrillator system are the defibrillator, which provides the voltage pulse, and the electrodes, which deliver the voltage pulse to the patient.

Prior art external defibrillator electrodes consist of a paddle having an electrode face electrically connected to the defibrillator by a cable. A conductive gel on the electrode face lowers the electrical resistance between the electrode and the patient. Disposable defibrillator electrodes are typically packaged with the gel pre-applied to the electrode face. Adhesive holds the electrodes in place on the patient. With standard reusable electrodes, on the other hand, the user must apply the gel before placing the electrodes on the patient. Handles on the back side of the electrode paddles enable the user to place the electrodes at the desired sites on the patient to hold the electrodes against the patient's skin.

SUMMARY OF THE INVENTION

One drawback of prior art defibrillator systems is the number of steps required to deploy the electrodes. Because defibrillators are used primarily in emergency situations, deployment and operation of defibrillator electrodes should be quick, easy and reliable. Prior art disposable defibrillator electrodes, however, require the following steps for deployment prior to delivery of the defibrillation pulse: connection of a cable to the defibrillator; inevitably, untangling of the cable; removal of the electrodes from their package; removal of the release liner covering the conductive gel over each electrode face and any adhesive surrounding the electrode; visual inspection of each electrode to determine whether it is usable; and application of the electrodes to the patient. Each of these steps takes time, and time is of the essence when trying to save a patient's life.

Furthermore, if a visual inspection or actual defibrillation attempt shows that either electrode is inoperative due to deterioration of the conductive gel, a broken conductor in the cable, a broken connection between the cable and the electrode, etc., then the deployment process must begin again, wasting even more time. What is needed, therefore, is a defibrillator system providing an indication of the condition of the defibrillator and defibrillator electrodes before deployment and placement on the patient.

Patient simulation units are available to test the operation of external defibrillators. Typically, the defibrillator output cable, i.e., the conductors leading to the electrodes, is connected to the simulation unit input. The defibrillator is then discharged as if the cable were attached to electrodes mounted on a patient. The simulation unit measures the defibrillator output pulse and gives an indication of the operating condition of the defibrillator. Because the defibrillator electrodes are not part of the test circuit, however, the simulation unit does not give any indication of electrode condition. Moreover, performing the test with patient simulation units adds to the burden of highly paid medical personnel, thereby raising the costs of the patient's care. What is needed, therefore, is a defibrillation system condition indicator that tests the electrodes and perhaps other parts of the defibrillator system automatically while the defibrillator is not in use.

This invention provides a defibrillator and electrode system that gives the user a visible and/or audible indication of the condition of the electrodes and other parts of the defibrillator system prior to deployment of the electrodes and use of the defibrillator. In a preferred embodiment of the method of this invention, a patient simulation and analyzer circuit within the defibrillator periodically tests the condition of the system and provides the user with a visual indication of the system's condition. One preferred embodiment of an electrode system useful for practicing this invention comprises a flexible substrate having a folded, undeployed position and an extended, deployed position. The substrate supports an electrode, an electrode tester conductive pad, and the electrical connections between the defibrillator and the electrode and between the conductive pad and the patient simulation and testing circuit. In its undeployed position, the electrode contacts the conductive pad to complete a circuit from the defibrillator, through the electrode to the patient simulation circuit.

In another preferred embodiment of an electrode system, the flexible substrate has a rolled or wound undeployed position and an unrolled or extended deployed position. The substrate supports a pair of electrodes, a pair of electrode tester conductive pads, and the electrical connections between these elements and the defibrillator and patient simulation circuits. In the substrate's undeployed position, the electrodes contact their respective conductive pads to complete a circuit from the defibrillator, through the electrodes to the patient simulation circuit.

The invention is explained in more detail below with reference to the drawings.

BRIEF DESCRIPTION OF THE DRAWINGS

FIG. 3 is an elevational view of an electrode system according to a preferred embodiment of this invention.

FIG. 4 is an exploded view of the electrode of FIG. 3.

FIG. 10 is a side cross-sectional view of the embodiment of FIG. 8, prior to deployment.

FIG. 11 is a side cross-sectional view of the electrode system of FIG. 10 with the electrodes partially deployed.

DETAILED DESCRIPTION OF THE PREFERRED EMBODIMENT

Figure 1:
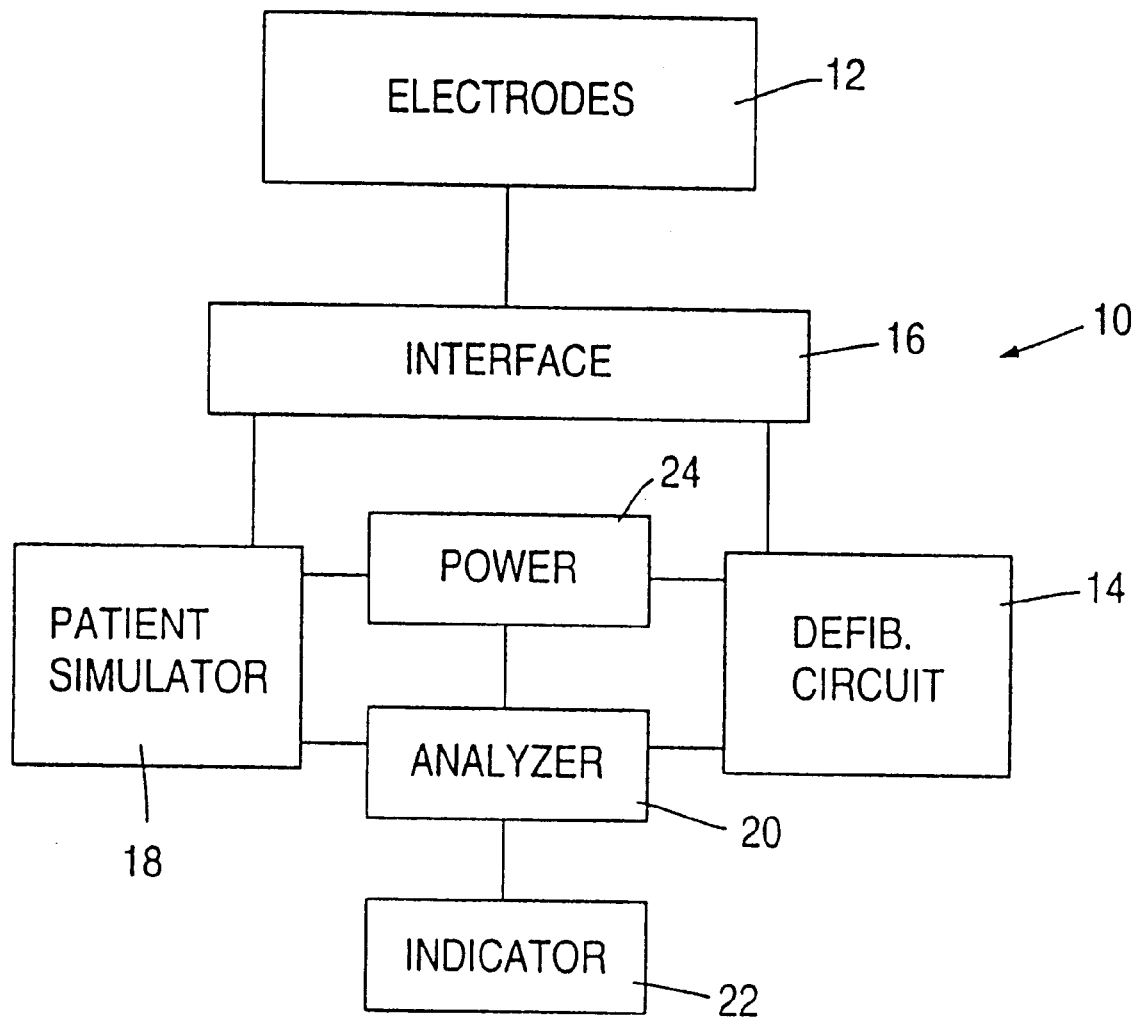
FIG. 1 shows a block diagram of a defibrillator system according to this invention.

FIG. 1 is a block diagram demonstrating the method and apparatus of this invention as applied to a defibrillator system. The defibrillator system 10 includes two or more electrodes 12 selectively connected to a standard defibrillator circuit 14 through an electrode interface 16. The defibrillator circuit applies a therapeutic voltage or current pulse to a patient through the electrodes under conditions controlled by logic within or associated with the circuit. The defibrillator may also receive information regarding the patient's heart activity from the electrodes in the form of ECG signals. The electrodes may be configured as described below or, alternatively, may be any defibrillator electrodes known in the art.

A patient simulator 18 is also selectively connected to the electrodes through interface 16. A defibrillator system analyzer 20 connected to the defibrillator circuit 14 and the patient simulator 18 controls the operation of the defibrillator circuit 14 during a test procedure, receives test information through the patient simulator 18, analyzes the test information, and indicates the test results via indicator 22. A power source 24 supplies power to the system.

The operation of the system of FIG. 1 is as follows. The system may be used to test the ability of the defibrillator circuit and electrodes to deliver a defibrillation pulse to a patient. Conductors leading from at least two electrodes are connected to the defibrillator circuit via an electrode interface. The electrode surfaces themselves, i.e., the portion of the electrodes that would be mounted on the patient during normal operation of the defibrillator, are electrically connected to the patient simulator, also via the electrode interface. A defibrillator test pulse is delivered from the defibrillator circuit to the electrodes, and the effect of the test pulse is measured at the patient simulator by the analyzer. The test pulse may be a voltage pulse of any magnitude, including but not limited to voltage magnitudes used for actual defibrillation. In that case, the analyzer will measure the current flowing through the patient simulator. The test pulse may also be a current pulse of any magnitude, in which case the analyzer will measure the voltage across the patient simulator. Other suitable tests will be apparent to those skilled in the art.

If the current or voltage measured at the patient simulator by the analyzer is below a predetermined threshold, the analyzer activates the indicator to show that the defibrillator is not operable. The indicator may be a visible indicator such as a light or a written message on a display, an audible sound, or any other suitable means of communicating an inoperable condition to the user.

The system may also be used to test the response of the logic portion of the defibrillator circuit to a signal originating with the patient. As in the other test, conductors leading from at least two electrodes are connected to the defibrillator circuit via an electrode interface. The electrode surfaces themselves, i.e., the portion of the electrodes that would be mounted on the patient during normal operation of the defibrillator, are electrically connected to the patient simulator, also via the electrode interface. A signal substantially similar to an ECG signal derived from a patient in ventricular fibrillation is generated by the patient simulator and delivered to the defibrillator circuit via the electrodes and electrode interface. In normal operation, the defibrillator should deliver a defibrillation pulse to the patient in response to such an ECG signal.

The analyzer monitors the output of the defibrillator circuit logic to the test ECG signal. If the defibrillator circuit logic fails to indicate that a defibrillation pulse is required, then the analyzer activates the indicator to show that the defibrillator is not operable. Again, the indicator may be a visible indicator such as a light or a written message on a display, an audible sound, or any other suitable means of communicating an inoperable condition to the user.

The ECG test may also be used to determine the response of the defibrillator circuit to a normal (non-fibrillating) ECG signal from a patient. As in the other tests, conductors leading from at least two electrodes are connected to the defibrillator circuit via an electrode interface. The electrode surfaces themselves, i.e., the portion of the electrodes that would be mounted on the patient during normal operation of the defibrillator, are electrically connected to the patient simulator via the electrode interface. A signal substantially similar to an ECG signal derived from a patient with a normal ECG, i.e., not in ventricular fibrillation, is generated by the patient simulator and delivered to the defibrillator circuit via the electrodes and electrode interface. In normal operation, the defibrillator should not deliver a defibrillation pulse to the patient in response to such an ECG signal.

The analyzer monitors the output of the defibrillator circuit logic to the test ECG signal. If the defibrillator circuit logic indicates that a defibrillation pulse is required, then the analyzer activates the indicator to show that the defibrillator is not operable. As with the other tests, the indicator may be a visible indicator such as a light or a written message on a display, an audible sound, or any other suitable means of communicating an inoperable condition to the user.

An indication that the defibrillator is not operable as a result of any of these tests could mean that there is a problem with the electrodes, the conductive gel on the electrodes, the electrode interface, and/or the defibrillator circuit itself. Therefore, if any test fails, the user may replace the electrodes and/or the electrode interface and run the test again. If the test indicates that the defibrillator system is now operable, then the problem was in the electrodes and/or electrode interface.

The analyzer can also be used to monitor the power level of the battery in a battery-operated defibrillator. If the battery level falls below a predetermined minimum, the analyzer activates the indicator to show that the defibrillator is not operable because of low battery level.

The frequency of any of these tests may be chosen to meet the system's requirements. For example, the power required for the defibrillator pulse tests may be so high that the frequency of this test must be limited in order to preserve battery life in battery-operated defibrillators. At the other extreme, the analyzer could monitor battery level continuously.

Figure 2:
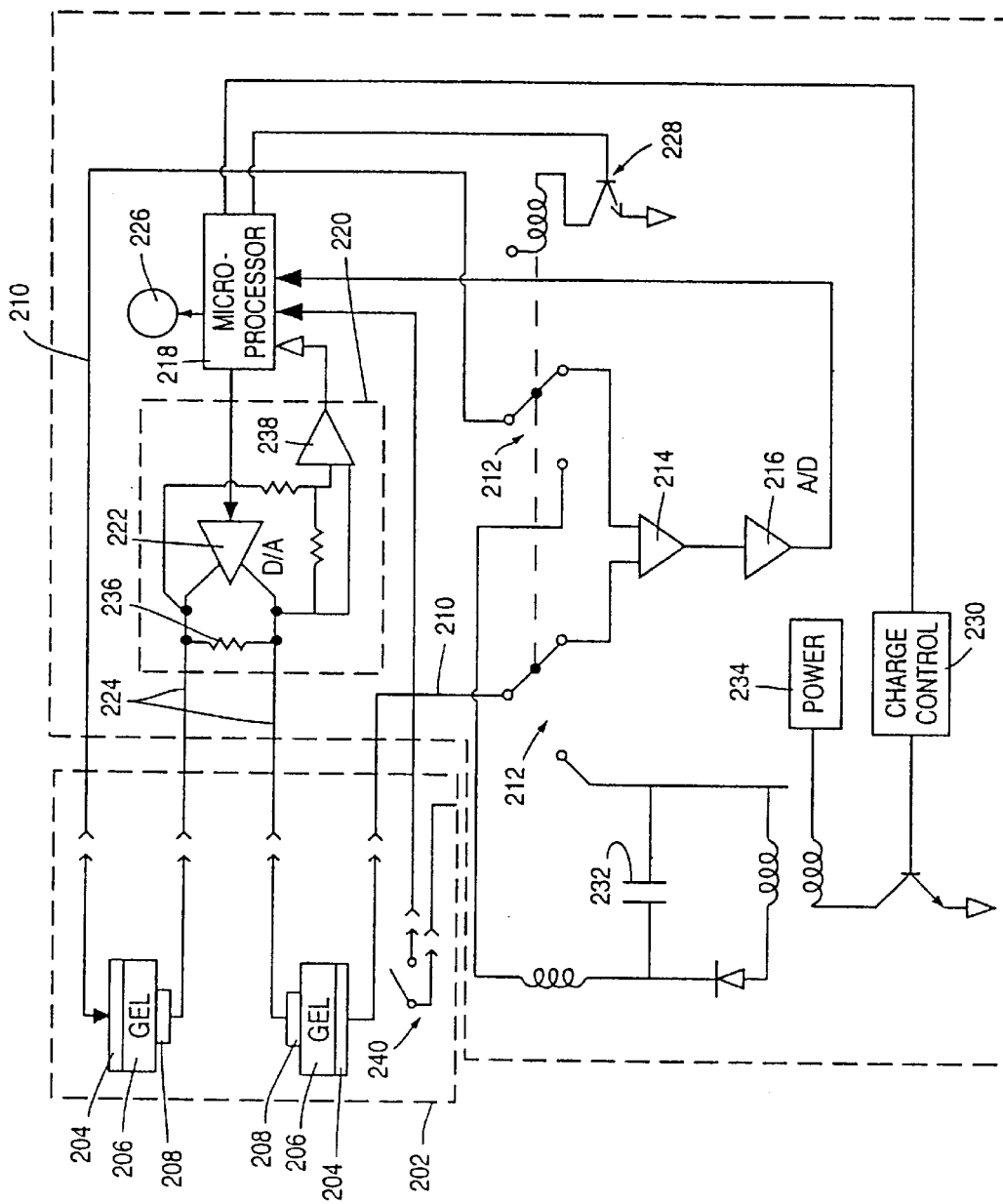
FIG. 2 is a schematic circuit diagram of the defibrillator system of this invention.

FIG. 2 is a circuit schematic showing one way of implementing the principal elements of the defibrillator system of the preferred embodiment. The portion of the schematic corresponding to the electrodes and electrode interface blocks of FIG. 1 is enclosed by a dotted line 202 and is referred to as the electrode apparatus or electrode system. The electrode apparatus 202 includes a pair of electrodes 204, conductive gel layers 206 covering the electrodes, and a pair of test pads or contacts 208 shown here to be in electrical contact with gel layers 206.

Electrodes 204 connect to a standard defibrillator circuit via conductors 210. In the circuit state shown here, the system is set to monitor patient ECG signals as if the electrodes were attached to a patient. In this monitoring state, switches 212 send the incoming signal from the electrodes through a preamp 214 and an A/D converter 216 for preprocessing before forwarding the signal to system microprocessor 218. Microprocessor monitors the received ECG signals and compares them to stored patterns or other criteria to distinguish normal patient ECG patterns from ECG patterns requiring action by the defibrillator system, as discussed below.

When configured as shown in FIG. 2, i.e., so that electrodes 204 are in electrical contact with test pads 208, the system is in test mode. The defibrillator system of this invention has a patient simulation and test circuit 220 to monitor the condition and integrity of the system prior to deployment of the electrodes and application of the electrodes to a patient. Periodically, microprocessor 218 sends a series of test signals to D/A converter 222, which converts the signals to their analog equivalent and transmits the signals to test pads 208 via conductors 224. Electrodes 204 retrieve the test signals as if the test signals were actual patient ECG signals and sends the signals back to the microprocessor through the ECG monitor circuit described above.

Preferably, the test signals are of at least two types: normal patient ECG waveforms, and ECG waveforms indicating a therapeutic pulse is required. The microprocessor analyzes the test signals as if they were actual patient ECG signals and decides whether or not to apply a therapeutic pulse to the electrodes. In ECG test mode, however, the actual pulse is not generated or applied. Rather, the microprocessor examines its own decision to determine if it was correct. If the outgoing ECG test signal from the microprocessor to the D/A converter was a normal ECG waveform and the microprocessor determines from the incoming test ECG signal that a therapeutic pulse is required, the system is faulty, and the microprocessor indicates the fault on a fault indicator 226. Likewise, if the outgoing ECG test signal from the microprocessor to the D/A converter was an ECG waveform indicating the need for a therapeutic pulse and the microprocessor determines from the incoming test ECG signal that a therapeutic pulse is not required, the system is faulty, and the microprocessor indicates the fault on a fault indicator 226. If, on the other hand, the microprocessor determines correctly the required course of action, the fault indicator is not activated.

If the system passes the ECG tests, it then performs a defibrillator test by generating a pulse through its normal pulse generating circuitry and sending the pulse to the electrodes 204. To initiate the pulse test, the microprocessor sends a charge command to a charge controller 230, which begins charging capacitor 232 in a known manner from power supply 234. When the charge on capacitor 232 has reached the required level (either the charge level required for normal operation or some other test charge level), switch relay 228 moves switches 212 to their other position. This switch position permits the pulse circuit to discharge the capacitor to deliver a damped sinusoidal shock to the electrodes.

The pulse transmitted by the electrodes through conductive gel layers 206 to test pads 208 is monitored by the test circuit 220 across a patient load simulator 236. The signal is reduced by a divider circuit and sent to microprocessor 218 via A/D converter 238. If the pulse received by the microprocessor does not meet predetermined criteria (such as voltage levels and signal waveform shape), the microprocessor indicates a system fault by activating fault indicator 226. So long as the system passes the tests, the tests are repeated periodically until the electrodes and their gel layers are removed from test pads 208 as determined by a deployment detector 240.

FIGS. 3 and 4 show an electrode apparatus according to a preferred embodiment of this invention. As shown in FIGS. 3 and 4, the electrode apparatus 40 has a relatively stiff electrode body 45 attached to a flexible substrate 42 with a medical grade adhesive. In this embodiment, substrate 42 is a polymer such as polyester or Kapton, approximately 3 mils thick. The length of substrate 42 depends on the requirements of the application. Electrode body 45 is preferably made from a light-weight, closed-cell foam approximately 25 mils thick.

An electrode disk 44 is disposed within electrode body 45. Electrode disk 44 is preferably a circular piece of metal foil, such as 3 mil tin, approximately 80 $cm^2$ in area, attached to substrate 42 with a suitable medical grade adhesive. Electrode disk 44 is covered with a layer of conductive gel 51 in a known manner. The thickness of gel layer 51 is 25 mils to make its top surface approximately even with the surrounding electrode body surface. Medical grade adhesive is disposed in adhesive area 52 on the top surface of electrode body 45 surrounding the opening 53 for electrode disk 44.

A first conductor 46 and a first electrical attachment pad 48 are formed on, or attached to, flexible substrate 42. Conductor 46 and electrical attachment pad 48 are preferably 3 mil tin foil formed integrally with electrode disk 44 and attached to substrate 42 with adhesive. A second conductor 43, a second electrical attachment pad 41 and a test pad 38 are formed on, or attached to, substrate 42. Conductor 43, attachment pad 41 and test pad 38 are also preferably formed as an integral piece of metal foil attached to substrate 42 with adhesive.

An insulating cover 47 is adhesively attached over substrate 42 and conductors 43 and 46. Cover 47 has a silicon release coating on its top side. Openings 49 and 37 are formed in cover 47 so that attachment pads 48 and 41, respectively, can make electrical contact with a connector, as described below. An additional opening 39 is formed in cover 47 so that test pad can make electrical contact with electrode 44 through gel 51, also as described below.

Figure 5:
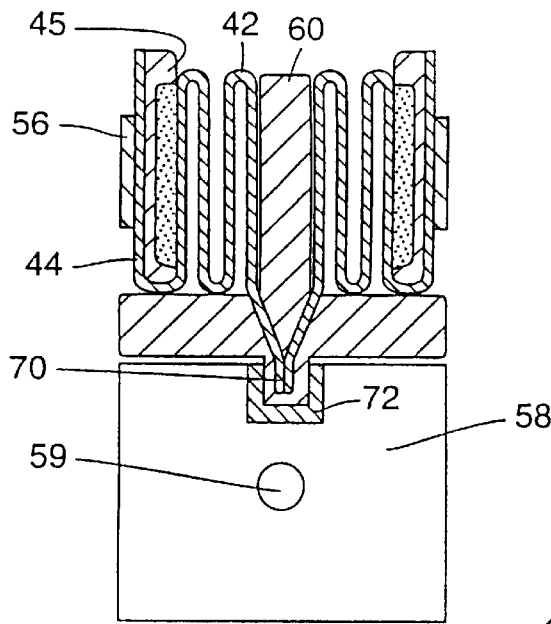
FIG. 5 is a side cross-sectional view of a defibrillator electrode system according to a preferred embodiment, prior to deployment.
Figure 6:
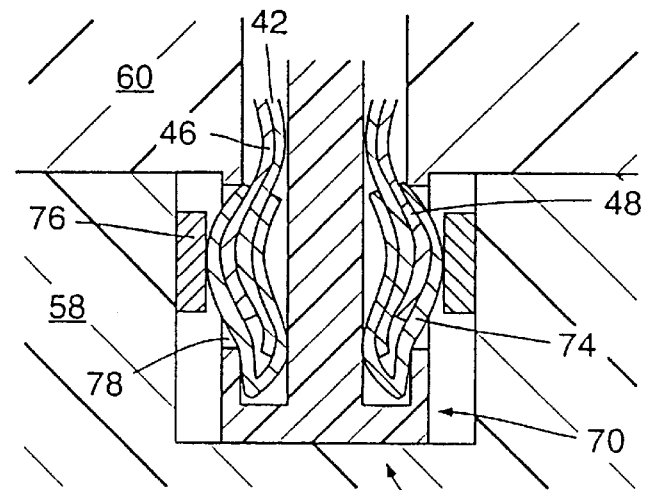
FIG. 6 is a cross-sectional view of a connector between an electrode system and an instrument.
Figure 7:
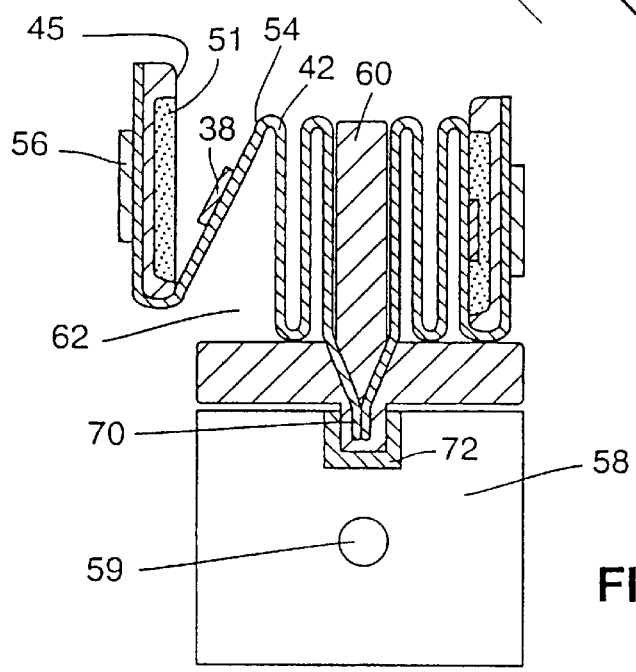
FIG. 7 is a side cross-sectional view of the defibrillator electrode system of FIG. 5 with one electrode partially deployed.

In FIGS. 5–7, a pair of the electrodes shown in FIGS. 3 and 4 are mounted in a retainer for use with a defibrillator system. FIG. 5 shows the electrodes in a predeployment storage position. In this position, the flexible substrate 42 of each electrode is folded in an accordion fashion and placed in retainer 60.

The portion of substrate 42 on which the attachment pads 41 and 48 are located extends into a retainer connector area 70 for electrical attachment to a corresponding connector 72 on the defibrillator 58. FIG. 6 shows the details of one embodiment of the connectors for attachment pads 48 on the two electrode apparatuses. The same arrangement may be used for attachment pads 41.

Metal crimps 74 at the end of substrate 42 make electrical contact with attachment pads 41 and 48. The crimps 74 partially extend through openings 78 in the connector portion 70 of retainer 60. When the retainer connector portion is inserted into the connector portion of the defibrillator 58, crimps 74 make electrical contact with defibrillator contacts 76. The resilient action of the crimps 74 also provide the mechanical attachment of retainer 60 to defibrillator 58. The contacts 76 for each electrode and for each test pad are connected to the defibrillator electronics in a known manner.

The test pads 38, their associated conductors 43, their attachment pads 41, and the retainer connector 70 serve as the interface between the electrodes and a patient simulator circuit within defibrillator 58 during the defibrillator system tests described above. An indicator 59 such as a light or an audible annunciator is provided to inform the user of test results.

Likewise, the conductors 46 and attachment pads 48 on the substrates are the interface between the electrodes and the defibrillator for delivery of the defibrillating voltage pulse and/or for monitoring of the electrical activity of the patient's heart during normal operation of the defibrillator. The positions of the electrode apparatus during the two operational modes will be explained with reference to FIGS. 5 and 7.

In the folded position shown in FIG. 5, the conductive gel 51 covering the electrode disk 44 of each electrode apparatus lies in electrical contact with its respective test pad 38. This contact closes the circuit going from one electrode through the patient simulation circuit to the other electrode so that the patient simulation tests can be performed.

Also, in the folded position shown in FIG. 5, the adhesive surrounding the electrode disk lies against an area 54 on the top surface of substrate 42. The top surface of substrate 42 is coated with a suitable release coating such as silicon in at least release area 54. The release coating enables the adhesive to peel away from substrate 42 during deployment of the electrode, as discussed below. The covering action of the substrate over the conductive gel also helps keep the conductive gel from drying out during storage. A handle 56 attached to the back side of electrode body 45 lies in position in which it can be grasped by a user during deployment of the electrodes.

FIG. 7 demonstrates deployment of the electrodes. As shown in FIG. 7, the user pulls electrode body 45 out of retainer 60 by grasping handle 56. As it moves out of the retainer, the electrode disk 44 and its conductive gel layer 51 peel away from substrate surface 42. Movement of the conductive gel layers 51 of the electrodes away from their respective test pads 38 breaks the circuit through the patient simulator. After removal from the retainer, the electrodes may be placed on a patient and used for monitoring the patient's heart activity and for applying therapeutic electrical pulses in the usual manner.

Figure 8:
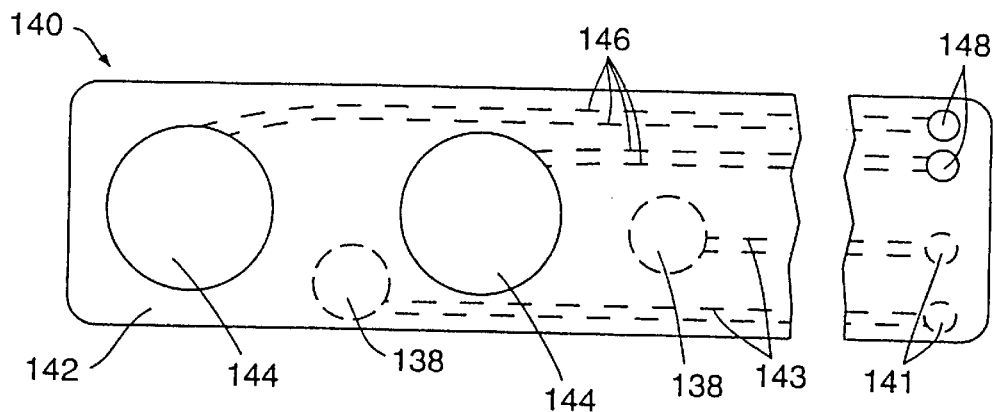
FIG. 8 is an elevational view of an alternative embodiment of the electrode system of this invention.
Figure 9:
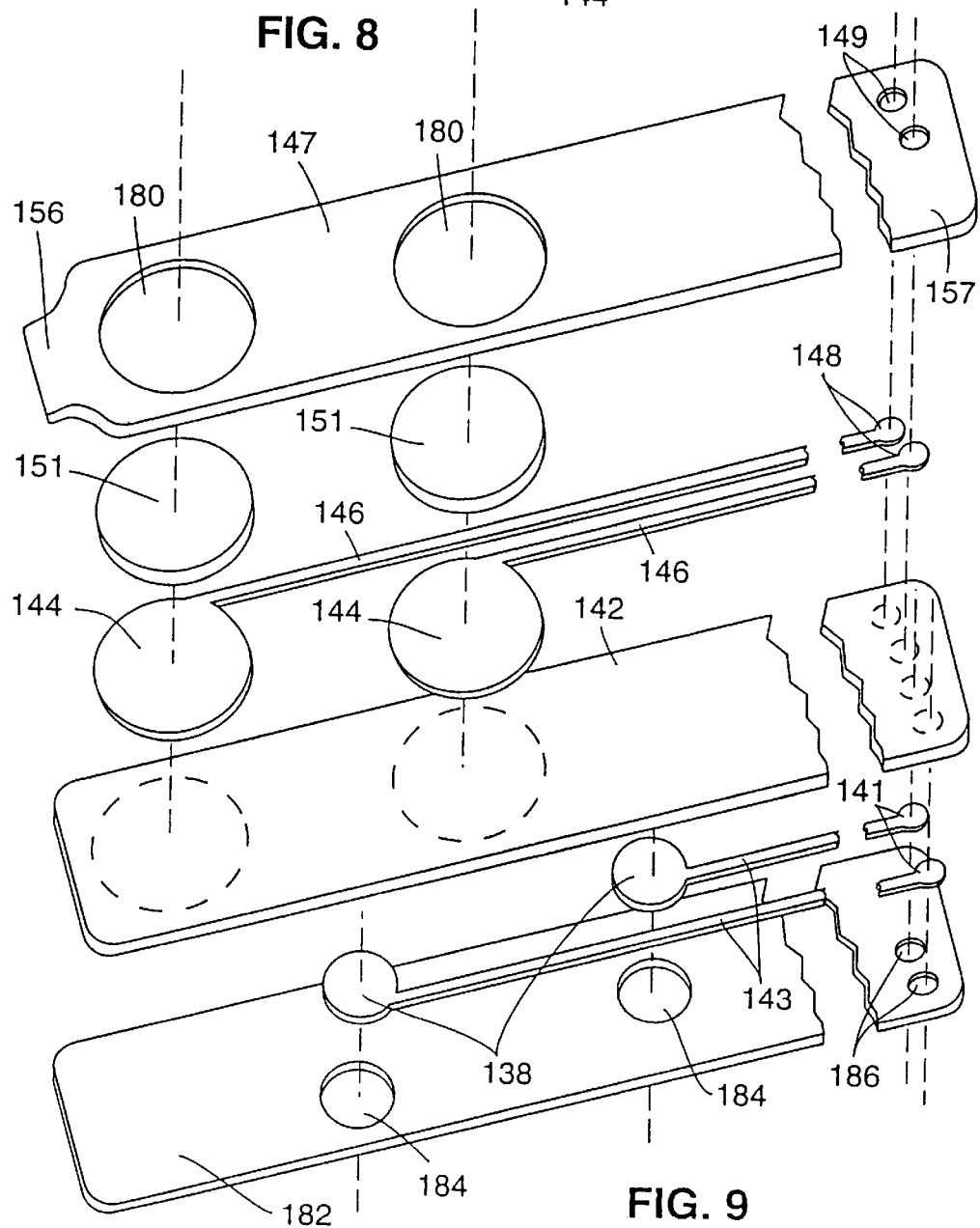
FIG. 9 is an exploded view of the electrode system of FIG. 8.

FIGS. 8–11 show an alternative embodiment of this invention. As shown in FIGS. 8 and 9, the electrode apparatus 140 has a flexible body or substrate 142, preferably formed from 1/16" closed cell foam. A backing layer 182 is attached to the underside of substrate 142 with a medical grade adhesive. Backing layer 182 may be formed from Tyvek or any other suitable material.

The underside of backing layer 182 is coated with a silicon release material. A pair of test pads 138 are adhesively attached to the top of backing layer 182 over a pair of openings 184 whose diameters are slightly smaller than the diameters of test pads 138. Openings 184 provide access to test pads 138 from the underside of backing layer 182.

Conductors 143 lead from test pads 138 to attachment pads 141. Openings 186 beneath attachment pads 141 have diameters slightly smaller than the diameters of attachment pads 141. Each set of test pad, conductor and attachment pad is preferably formed from a single piece of tin metal foil 3 mils thick.

A pair of electrodes 144 are adhesively attached to the top of substrate 142. Conductors 146 lead from electrodes 144 to attachment pads 148. Each set of electrode, conductor and attachment pad is preferably formed from a single piece of tin metal foil 3 mils thick. The surface area of each electrode is preferably 80 cm². A layer of conductive gel 151 covers each electrode. The thickness of the conductive gel layer is preferably 25 mils.

An insulating cover 147 is attached to the top side of substrate 142 with medical grade adhesive. Cover 147 has openings 180 for the electrodes and openings 149 for the attachment pads. Openings 180 have diameters slightly smaller than the diameters of their respective electrodes, and openings 149 have diameters slightly smaller than their respective attachment pads. Medical grade adhesive covers all of the top surface of cover 147 except for handle area 156 and connector area 157 for attachment of the electrode apparatus to a patient.

FIGS. 10 and 11 show the electrode apparatus of this embodiment mounted in a retainer. As seen in FIG. 10, prior to deployment, the electrode apparatus is wound around a spool-shaped retainer 160 mounted on top of a defibrillator 158. The portion of the electrode apparatus on which the attachment pads 141 and 148 are located extend into the center of the retainer spool where they make electrical connection with conductors (not shown) that connect to the defibrillator connector 172. The metal crimps shown in FIG. 6 may be used for this purpose. A protective cover 164 may be kept over retainer spool 160 until the electrodes are to be deployed.

In the undeployed state shown in FIG. 10, the conductive gel layers 151 and the adhesive coating on cover layer 147 face the inward toward the center of the retainer spool, and the release coating on the underside of backing layer 182 faces outward from the center. Thus, when the electrode apparatus is wound about itself, the conductive gel layers 151 and the adhesive coating on the cover layer lie against the silicon release coating of the backing layer 182. Also, the conductive gel layers 151 of each electrode lie in electrical contact against their respective test pads 138, as shown. This contact closes the circuit going from one electrode through the patient simulation circuit to the other electrode so that the patient simulation tests can be performed. An indicator 159 such as a light or an audible annunciator is provided to inform the user of test results.

To deploy the electrode apparatus of this embodiment, the protective cover 164 is removed, and the electrode apparatus is unwound from retainer spool 160 by pulling on handle or tab 156, as shown in FIG. 11. The release coating on backing layer 182 permits the conductive gel layers 151 and the adhesive on cover layer 147 to peel away. Movement of the conductive gel layers 151 of the electrodes away from their respective test pads 138 breaks the circuit through the patient simulator. The electrode apparatus is then applied to the patient and used for monitoring the patient's heart activity and for applying therapeutic electrical pulses in the usual manner.

The electrode apparatus and spool retainer remain attached to the defibrillator during use. The conductors 146 and attachment pads 148 provide the electrical connection between the electrodes 144 and the defibrillator for delivery of the defibrillating voltage pulse and/or for monitoring of the electrical activity of the patient's heart. After use, the retainer spool and the electrode apparatus it houses can be discarded and replaced with a new electrode set.

Modifications may be made to the described embodiments without departing from the scope of the invention. For example, other electrode configurations may be used with the test apparatus of this invention so long as an appropriate electrode interface is provided. When selecting electrode materials, it should be remembered that repeated tests could cause corrosion of the electrodes and/or test pads if the tests are not charge-balanced. In addition, while in the preferred embodiment the defibrillator runs the electrode integrity tests, it should be understood that a separate test unit may be used instead. The electrodes would then have to be disconnected from the test unit and connected to a defibrillator before actual use. Also, while this invention has been described in the context of defibrillators and defibrillator electrodes, it should be understood that the invention applies to medical electrodes used with other instruments, such as ECG monitors.

Other modifications will be apparent to those skilled in the art.

What is claimed is:

1. A method for maintaining a defibrillator comprising the following steps:
    periodically delivering a test pulse in a defibrillator from an energy source through conductors to a patient simulator within the defibrillator automatically without external activation;
    analyzing a signal detected at the patient simulator to determine a condition of the defibrillator; and
    providing an indication of the condition of the defibrillator.

2. The method of claim 1 wherein the delivering step is controlled by a microprocessor.

3. The method of claim 1 further comprising the step of periodically delivering a test ECG signal in the defibrillator from a test signal source to a patient simulator within the defibrillator automatically without external control.

4. The method of claim 3 further comprising analyzing the test ECG signal to determine a condition of the defibrillator.

5. A method for maintaining a defibrillator prior to deployment of the defibrillator, the method comprising the following steps:

(1) performing a defibrillator self-test automatically without external activation; and (2) providing an indication of a result of the defibrillator self-test.

6. The method of claim 5 wherein step (1) is performed periodically.

7. The method of claim 5 wherein steps (1) and (2) are performed periodically.

8. The method of claim 5 wherein step (1) comprises delivering a test pulse from an energy source to a patient simulator within the defibrillator.

9. The method of claim 8 wherein step (1) further comprises analyzing a signal received at the patient simulator to determine a condition of the defibrillator.

10. The method of claim 5 wherein step (1) comprises delivering a test ECG signal from a test signal source.

11. A method for maintaining a defibrillator prior to deployment of the defibrillator, the method comprising the following steps:

(1) performing a plurality of self-tests automatically without external control, the self-tests comprising a first self-test being performed at a first frequency and a second self-test being performed at a second frequency; and (2) providing an indication of a result at least one of the first and second self-tests.

* * * * *